United States Patent [19]
Zilber

[11] Patent Number: 4,955,859
[45] Date of Patent: Sep. 11, 1990

[54] HIGH-FRICTION PROSTATIC STENT
[75] Inventor: Serge Zilber, Conyers, Ga.
[73] Assignee: C. R. Bard, Inc., Murray Hill, N.J.
[21] Appl. No.: 376,822
[22] Filed: Jul. 7, 1989
[51] Int. Cl.$^5$ .............................................. A61M 5/00
[52] U.S. Cl. ........................................ 604/8; 604/280
[58] Field of Search .................. 604/8, 43, 280, 175, 604/164, 282, 96; 128/343

[56] References Cited
U.S. PATENT DOCUMENTS

| | | | |
|---|---|---|---|
| 3,738,365 | 6/1963 | Schulte | 604/8 |
| 3,938,529 | 2/1976 | Gibbons | 604/8 |
| 4,636,346 | 1/1987 | Gold et al. | 604/280 |
| 4,674,506 | 6/1987 | Alcond | 604/8 |
| 4,787,884 | 11/1988 | Goldberg | 604/8 |

Primary Examiner—Robert A. Hafer
Assistant Examiner—Kerry Owens
Attorney, Agent, or Firm—Jones, Askew & Lunsford

[57] ABSTRACT

A urethral stent is disclosed for the nonsurgical management of bladder outlet obstruction caused by an enlarged prostate. The stent is sufficiently rigid to provide support to assure patency of an intact but contracted urethral lumen but is sufficiently flexible to accommodate the natural anatomical bend of the prostatic urethra. The stent further includes means for frictionally engaging the urethral walls to anchor the device within the prostatic urethra and to prevent migration back into the bladder or down the urethra. When the need arises, the stent is easily and nonsurgically removed from the prostatic urethra.

6 Claims, 2 Drawing Sheets 4,955,859

HIGH-FRICTION PROSTATIC STENT

TECHNICAL FIELD

The present invention relates generally to anatomical stents for providing support to assure patency of an intact but contracted lumen, and relates more specifically to a prostatic stent for the nonsurgical management of bladder outlet obstruction, such as in the case of prostatic hyperplasia or hypertrophy.

BACKGROUND OF THE INVENTION

Bladder outlet obstruction is one of the most commonly encountered disorders in urology. The most frequently occurring anatomical cause of bladder outlet obstruction in males is enlargement of the prostate gland, either by hypertrophy or hyperplasia. The prostate is a chestnut-sized gland lying inferior to the bladder and surrounding approximately the first inch of the urethra. In older males, it is not uncommon for a progressive enlargement of the prostate to constrict the prostatic urethra. This condition, known as benign prostatic hyperplasia, can cause a variety of obstructive symptoms, including urinary hesitancy, straining to void, decreased size and force of the urinary stream, and, in extreme cases, complete urinary retention possibly leading to renal failure. A number of irritative symptoms may also be experienced, including urinary frequency and urgency, nocturnal incontinence, and discomfort.

When intervention is indicated, there has heretofore been no widely accepted alternative to surgery. The preferred surgical procedure is the transurethral resection, wherein a resectoscope is inserted through the external opening of the urethra, and an electrosurgical loop is employed to cut away sections of the prostate gland from within the prostatic urethra. However, many patients are poor candidates for transurethral resection. Contraindications for this surgery may include cardiac problems or inability to undergo anesthesia. Also, the patient may have elective reasons for needing to postpone surgery. Thus, there is a need to provide a mechanism for the management of bladder outlet obstruction in those patients where surgical intervention is inappropriate.

Efforts have been made to provide a nonsurgical modality for the management of bladder outlet obstruction resulting from prostatic hypertrophy and hyperplasia. One such example is found in U.S. Pat. No. 4,762,128, which discloses an expandable tubular urethral stent. The stent includes a perforated expandable central section comprised of a malleable metal to permit expansion of the central section and to hold its expanded configuration under pressure. The stent is adapted for transurethral insertion via the external opening of the urethra and for placement within a stenotic region of the urethral lumen caused by a hypertrophied prostate gland. When the stent is properly positioned, an expansion catheter is inflated within the stent, thereby causing the expandable central section of the stent to deform outwardly, thereby ensuring patency of the lumen.

However, the expandable stent of the aforementioned U.S. Pat. No. 4,762,128 has not gained widespread acceptance because of the fear that the tissue of the urethral walls, under pressure from the enlarged prostate, will penetrate the perforations of the expanded central section of the stent. The more the stent is expanded, the larger the perforations become, and the greater the pressure exerted between the expanded stent and the enlarged prostate. Under these conditions, the tissue of the urethral walls would tend to penetrate even more deeply into the perforations of the stent and thereby render the stent difficult, if not impossible, to remove without major surgery.

Another example of a nonsurgical modality for the management of bladder outlet obstruction is the Prostakath ® intraurethral catheter. This device comprises a short, gold-plated metal helix or spiral which is tapered at one end and terminates in a loop at the other. The metal spiral is endoscopically placed within the stenosed region of the prostatic urethra to reinforce the lumen. Again, however, this device has not gained widespread acceptance, largely because of concerns regarding encrustation of the metal spiral which may cause the spiral to adhere to the urethral walls, thereby necessitating surgery to remove the device. In addition, there have been reservations that the tip of the spring may cause bladder irritation. Finally, there have been concerns that attempts to remove the metal spiral by endoscopically pulling on its distal end may cause the spiral to unwind such that the sharp end of the wire lacerates the urethra.

SUMMARY OF THE INVENTION

As will be seen, the present invention overcomes these and other disadvantages associated with prior art modalities for the management of bladder outlet obstruction resulting from prostatic hypertrophy. Stated generally, the present invention comprises a stent for placement within the prostatic urethra to ensure patency of the urethra against the constrictive pressure of an enlarged prostate. The stent is easily installed and, should circumstances warrant, easily removed without the need for invasive surgical techniques.

Stated somewhat more specifically, the stent of the present invention includes an elongated body defining a passage therethrough. The body is dimensioned to be received within the patient's prostatic urethra and has a length sufficient to extend from the neck of the bladder to the verumontanum. Since the prostatic urethra has a natural bend of approximately forty-five degrees, the body of the stent must be sufficiently flexible to accommodate this anatomical bend without kinking. At the same time, however, the stent must be sufficiently strong to maintain patency of the urethra in response to constrictive forces exerted by the enlarged prostate. In one disclosed embodiment, this desired combination of strength and flexibility is achieved by embedding a helical steel spring within a body of relatively soft silicone rubber. In another disclosed embodiment, the combination of strength and flexibility is attained by a clad construction comprising a relatively rigid core of a comparatively high durometer silicone rubber coated with a softer outer jacket of relatively low durometer silicone rubber.

A stent disposed within the prostatic urethra is subjected to a variety of forces which tend to displace the stent. The bladder can exert a pressure of up to one hundred centimeters of water during voiding, which pressure tends to expel the stent from the urethra. Additionally, the normal slight contraction of the smooth muscle of the bladder neck upon completion of micturition tends to draw a stent into the bladder. It is also possible that normal body motions such as walking or running may tend to displace a stent within the urethra. To inhibit such possible migration, the stent of the present invention includes means for anchoring the stent within the prostatic urethra. To prevent migration of the stent down the urethra, a flange is formed at one end of the elongated stent body and is configured to engage the tapered neck of the bladder. The stent body further has a rough, textured surface for frictionally engaging the walls of the prostatic urethra, thereby to prevent the stent from migrating proximally into the bladder. In one disclosed embodiment, the frictional surface comprises a plurality of asperities molded onto the body of the stent. In another disclosed embodiment, the textured surface comprises a layer of velour fabric bonded to the exterior surface of the stent body.

To facilitate monitoring of the stent by conventional X-ray techniques, the stents of the disclosed embodiments are radiographically opaque. In the embodiment comprising a metal spring embedded in silicone rubber, the metal spring provides the requisite degree of radiographic opacity. In the clad construction of relatively hard and soft silicone rubbers, radiographic opacity is attained by intermixing a radiographically opaque substance such as titanium oxide or tantalum oxide with the silicone rubber.

The stent is positioned within the prostatic urethra with the conical flange disposed within the neck of the bladder and the opposite end of the stent body extending approximately to the verumontanum. The conical flange engages the bladder neck to prevent migration of the stent down the urethra, and the textured exterior surface of the stent frictionally engages the urethral walls to prevent migration of the stent into the bladder. The stent thus provides support to the prostatic urethra and ensures its patency.

Thus, it is an object of the present invention to provide an improved mechanism for managing bladder outlet obstruction resulting from an enlarged prostate.

It is a further object of the present invention to provide a mechanism for the management of bladder outlet obstruction in those patients where surgical intervention is inappropriate.

Another object of the present invention is to provide a prosthesis for ensuring the patency of the urethral lumen which is easily installed and, when the need arises, easily removed without major surgery.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
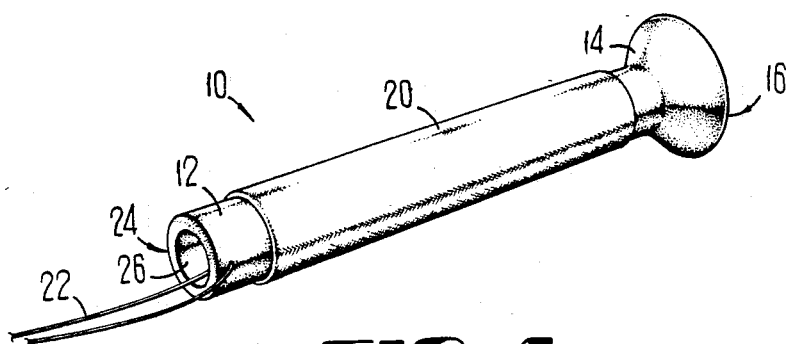
FIG. 1 is a perspective view of a stent according to a first disclosed embodiment of the present invention.
Figure 2:
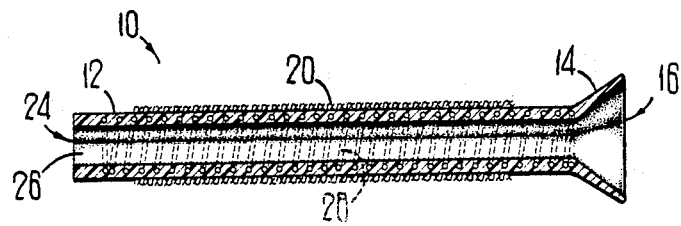
FIG. 2 is a cutaway view of the stent of FIG. 1.

Referring now to the drawings, in which like numerals indicate like elements throughout the several views, FIGS. 1 and 2 show a stent 10 according to a first embodiment of the disclosed invention. The stent 10 comprises a generally tubular body 12 having a frustoconically shaped flange 14 at its upper end 16. The stent 10 of the disclosed embodiment is formed from silicone rubber, though it will be appreciated that other appropriate materials may be used. The stent 10 further comprises a textured fabric outer layer 20 bonded to the tubular body 12 of the stent. In the disclosed embodiment, the textured fabric layer 20 is comprised of a Dacron ® velour of the type normally used in medical cardiovascular procedures. The velour is formed into an annular jacket, slipped over the body 12 of the stent 10, and bonded thereto. Optionally, the stent 10 may also comprise a filament 22 secured to the lower end 24 of the stent body 12 to facilitate insertion and positioning of the stent, in the manner to be further described below.

Referring now to FIG. 2, the stent 10 further comprises an axial lumen 26 running longitudinally therethrough. An internally positioned helical steel spring 28 surrounds the lumen 26 and extends from the upper end 16 of the stent to approximately one centimeter from the lower end 24 of the stent. The steel spring 28 reinforces the stent 10 while affording considerable flexibility to the stent, to the advantage hereinbelow described. The steel spring 28 provides the further advantage of rendering the stent 10 radiographically opaque, whereby the position of the stent within a patient may be monitored using conventional fluoroscopic techniques.

Figure 3:
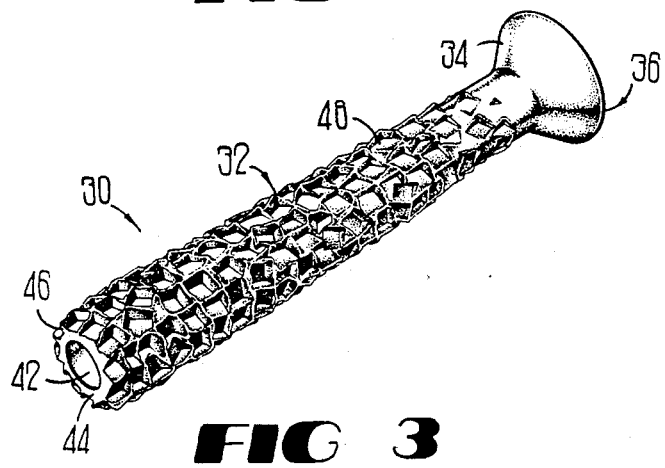
FIG. 3 is a perspective view of a stent according to a second disclosed embodiment of the present invention.
Figure 4:
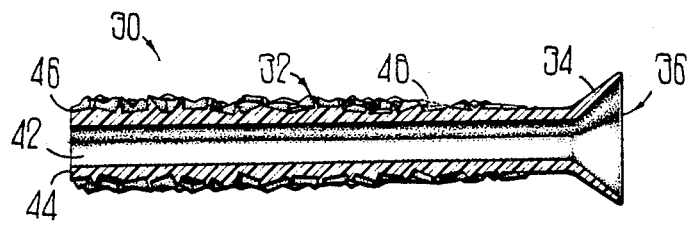
FIG. 4 is a cutaway view of the stent of FIG. 3.

FIGS. 3 and 4 disclose a stent 30 according to a second embodiment of the disclosed invention. Like the stent 10, the stent 30 comprises a generally tubular body 32 having a conical flange 34 at its upper end 36 and defining a lumen 42 therethrough. However, the stent 30 is a clad fabrication comprising a relatively high durometer inner liner 44 having a relatively low durometer outer jacket 46 formed thereupon. In the disclosed embodiment, the inner liner 44 is comprised of silicone rubber having a hardness of 80 on the Shore A durometer scale. The outer jacket 46 is comprised of silicone rubber having a Shore A hardness of about 40. The soft silicone rubber outer jacket 46 of the stent 30 has a roughened outer surface 48. In the disclosed embodiment, the silicone rubber comprising the inner lining 44 of the stent 30 is rendered radiographically opaque by mixing titanium oxide, tantalum oxide, or the like, with the silicone rubber.

Figure 5:
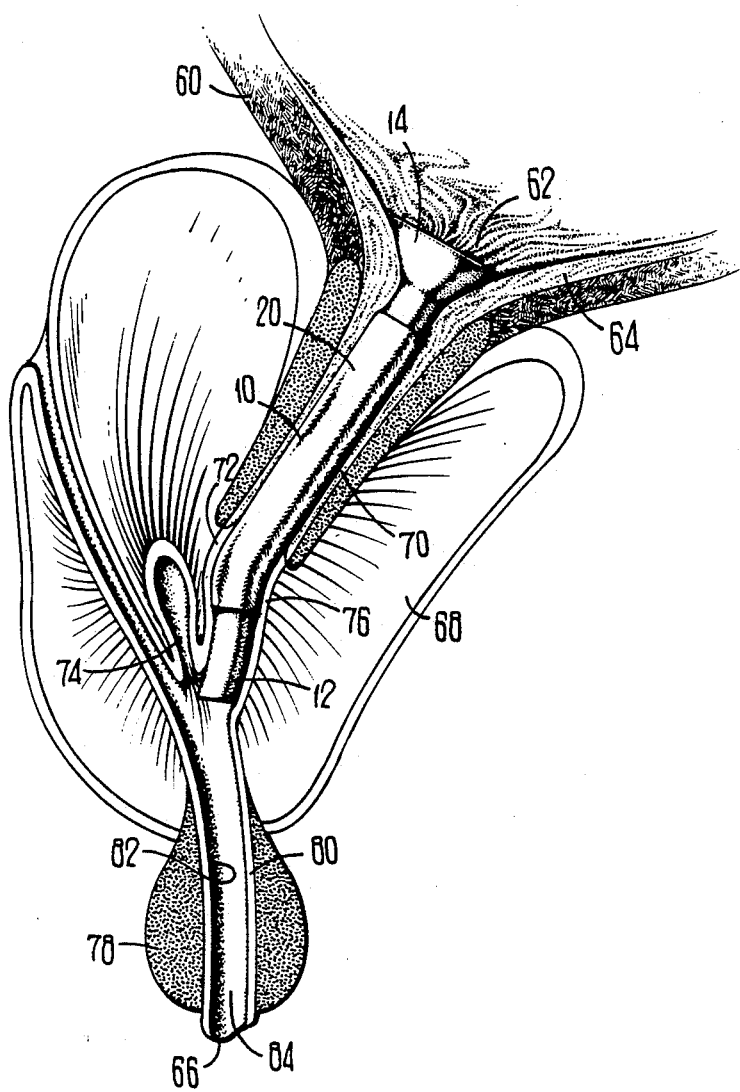
FIG. 5 is a sagittal plane view of a lower urinary tract depicting the stent of FIG. 1 disposed within the prostatic urethra.

The physiology of the environment within which the prostatic stent resides is well known and will be discussed here only briefly. With reference to FIG. 5, the bladder 60 has a tapered bladder neck 62 at its lower end surrounded by smooth musculature 64. The bladder neck 62 tapers into the urethra 66. Approximately the upper three or four centimeters of the urethra 66 are surrounded by the prostate gland 68. When the prostate gland 68 becomes enlarged as a result of hypertrophy or hyperplasia, the prostate exerts stenotic pressure on the prostatic urethra 70 and may partially or completely occlude the urethra.

On the posterior wall 72 of the urethra 66 at the approximate midpoint of the prostatic urethra 70 is a small projection, the verumontanum 74. The prostatic urethra 70 has a bend 76 therein in the sagittal plane and between the bladder neck 62 and the verumontanum 74 of approximately 45°; or, stated differently, the prostatic urethra forms an included angle of approximately 135°. Distal to the prostatic portion 70 of the urethra 66 is the external sphincter 78.

Other physiological features of the bladder 60 and urethra 66 are also relevant to the intended environment of the prostatic stents 10, 30 of the present invention. During micturition, the bladder 60 normally exerts an expulsive pressure of 40 cm/$H_2O$ within the prostatic urethra 70 and is capable of exerting a pressure of up to 100 cm/$H_2O$. Further, upon completion of micturition, the smooth bladder neck musculature 64 contracts slightly, which contraction tends to draw objects in the prostatic urethra 70 back into the bladder 60. Finally, the walls 80 of the urethra 66 have a mucosal layer 82 lining the lumen 84 of the urethra which is extremely slick.

It will thus be appreciated that the stents 10, 30 must be sufficiently flexible to accommodate the natural anatomical bend 76 of the prostatic urethra 70 without kinking. At the same time, however, the stents must be sufficiently strong to assure the patency of the urethral lumen 84 against the stenotic pressure exerted by an enlarged prostate 68. Further, the stents must be anchored in such a manner as to prevent migration of the stents, both proximally back into the bladder and distally down the urethra.

The desired combination of strength and flexibility is achieved in the stent 10 of the first embodiment by the incorporation of the internal helical steel spring 28. The spring 28 reinforces the lumen 26 of the stent 10 against radial compressive forces while permitting the degree of flexibility necessary to accommodate the anatomical bend 76 of the prostatic urethra 70. Similarly, the stent 30 affords the desired flexibility and strength by means of the relatively high durometer inner liner 44 which is sufficiently strong to withstand radial stenotic forces without collapsing, yet is sufficiently flexible to accommodate the anatomical bend 76.

The interrelation between the stent 10 and its intended environment will now be discussed. With the stent 10 disposed within the prostatic urethra, as depicted in FIG. 5, the conical flange 14 at the upper end 16 of the stent is disposed within the tapered neck 62 of the bladder 60. The lower end 24 of the stent 10 is disposed approximately at the verumontanum 74, and the body 12 of the stent flexes as necessary to accommodate the physiological bend 76 in the prostatic urethra 70. It will be appreciated that the stent 10 is of sufficient length that the stenotic pressure exerted by the enlarged prostate 68 cannot occlude the lumen 84 of the urethra 66 below the lower end 24 of the stent.

With the stent 10 thus positioned within the prostatic urethra 70, the conical flange 14 at the upper end 16 of the stent engages the tapered bladder neck 62, and the highfriction textured fabric layer 20 on the tubular body 12 of the stent 10 frictionally engages the walls 80 of the urethra 66. During micturition, the expulsive fluid pressure exerted by the bladder 60 tends to displace the stent 10 distally, that is, down the urethra 66. However, the stent is anchored against migration distally by the interference fit between the conical flange 14 and the tapered bladder neck 62. Similarly, upon completion of micturition, the normal contraction of the smooth bladder neck musculature 64 will grasp the flange 14 of the stent and tend to draw the stent into the bladder 60. However, the frictional engagement between the textured fabric outer layer 20 and the walls 80 of the urethra 66 is sufficient, despite the presence of the mucosal layer lining the lumen 84, to anchor the stent against such proximal migration.

The interrelation between the stent 30 of the second embodiment and its intended environment is similar to that of the stent 10 and is thus not illustrated separately. The high-durometer inner liner 44 is sufficiently pliable to accommodate the anatomical bend 76 of the prostatic urethra 70, while providing sufficient strength to resist the radial stenotic pressure exerted by the enlarged prostate 68 without occluding. The conical flange 34 at the upper end 36 of the stent 30 engages the tapered bladder neck 62 to anchor the stent against distal migration. The roughened exterior surface 48 of the outer jacket 46 frictionally engages the walls 80 of the urethra 66 to anchor the stent 30 against proximal migration in the same manner as hereinabove described with respect to the fabric outer layer 20 of the stent 10.

The manufacture of the stent 10 with integral steel spring reinforcing element will now be discussed. A dipping form in the shape of a rod having a reduced cylindrical portion and an outwardly flared enlarged portion is employed. The reduced cylindrical portion of the form will define the lumen of the stent, and the flared portion will define the conical flange. Prior to use, the dipping form is coated with a release coating of conventional formulation to facilitate the later removal of the completed stent from the form. The form is then dipped in liquid silicone rubber to form a first layer of material on the rod. The silicone rubber from which the stent 10 of the disclosed embodiment is constructed employs a room temperature vulcanization process. As soon as the first layer of silicone rubber has begun to set, the form is dipped again, thereby building up successive layers of silicone rubber. After two or three layers have been formed, the helical steel spring is inserted over the reduced cylindrical portion of the rod, and the form is dipped in the liquid silicone rubber again until the helical steel spring is completely encased and the thickness of the stent wall has reached the desired dimension. The annular jacket of velour fabric is then slipped over the body of the stent and bonded to the stent using the same room temperature vulcanization silicone rubber as was used to form the stent body. When the silicone rubber has cured, the stent is removed from the form.

The method of manufacturing the clad embodiment of the stent 30 will now be discussed. The inner liner 44 is molded from a silicone rubber having a hardness when cured of approximately 80 on the Shore A durometer scale. Titanium oxide or tantalum oxide are advantageously mixed with the silicone rubber from which the inner liner 44 is molded to render the stent 30 radiographically opaque. The inner liner is molded with a roughened outer surface to promote subsequent bonding with the outer jacket 46. When the molded inner liner 44 has cured, it is dipped into a quantity of liquid silicone rubber which has a Shore A hardness of about 40 when cured. When the inner liner is removed from the liquid silicone rubber, it is immediately placed in a fluidized bed containing pellets of acrylonitrilebutadiene-styrene ("ABS"). The pellets adhere to the uncured surface, and the surface is allowed to cure for approximately an hour. When the soft outer layer of silicone rubber has cured, the ABS pellets are peeled away from the stent, leaving asperities or irregularities in the spaces formerly occupied by the pellets. These asperities impart a roughened texture to the outer layer to provide the high-friction characteristics hereinabove described.

The procedures for fitting and installing the stents 10, 30 of the respective embodiments are substantially identical and will be discussed together. The first step in fitting a stent 10, 30 is the measurement of the patient's prostatic urethra 70. On the one hand, it is desirable to provide a stent which extends substantially the length of the prostatic urethra whereby occlusive pressure exerted by an enlarged prostate gland 68 will not obstruct the lower end of the stent. On the other hand, it is imperative that the stent not be so long as to interfere with the normal operation of the external sphincter 78, lest incontinence result. It has been found that optimum results are achieved when the stent is of a length sufficient to extend from the bladder neck 62 to the verumontanum 74. Thus, the first step in fitting a patient with a prostatic stent according to the present invention is to measure the distance from the bladder neck to the verumontanum.

Both the bladder neck 62 and the verumontanum 74 are easily identifiable physiological landmarks. The distance between these two structures can be measured either cystoscopically or using ultrasound equipment. Using a cystoscope, a sheath is introduced into the urethra 66 and worked past the external sphincter 78. The cystoscope is then inserted through the sheath to view the prostatic urethra 70. When the physician has located the verumontanum 74, a mark may be placed on the tube of the cystoscope outside the patient's body at the point where the cystoscope enters the sheath. The physician will then insert the cystoscope further up the prostatic urethra until the bladder neck 62 is located, and a second mark will be placed on the body of the cystoscope at the new point where the scope enters the sheath. By measuring the distance between the two points marked on the body of the cystoscope, the distance between the verumontanum and the bladder neck can be ascertained.

An alternate method of measuring the distance between the bladder neck and the verumontanum is to use conventional ultrasound equipment. Using an abdominal or external probe, the physician can visualize the bladder neck and verumontanum on the ultrasound monitor. Most modern ultrasound equipment will permit the distance between the verumontanum and bladder neck to be measured directly from the ultrasound monitor. A movable cursor is positioned on the ultrasound monitor at first one location and then the other, and the distance between the two cursor locations is computed automatically.

Once the distance between the bladder neck 62 and the verumontanum 74 has been measured using either of the aforementioned methods, the stent is trimmed to a length corresponding to that distance plus or minus two millimeters. For most applications, the resulting stent will range from 3.5 to 6.5 centimeters in length. An advantage of the stent 30 over the stent 10 is that the stent 30 of the all-silicone construction is infinitely trimable. In contrast, the stent 10 with integral helical spring 28 is trimable only up to the point on the stent body 12 where the metal spring begins, typically permitting adjustment in length of only about one centimeter. Thus, the stent 10 with integral metal spring reinforcement will need to be provided in variety of different lengths in one centimeter increments, ranging from about four centimeters to about seven centimeters in length. A stent 10 having a length which is less than one centimeter longer than the measured distance between the bladder neck and verumontanum will then be selected and trimmed to the desired dimension.

Once the stent 10, 30 has been trimmed to the appropriate length, it is ready for placement in the prostatic urethra. If the measurement of the prostatic urethra was taken using a cystoscope, a sheath will already be in place in the urethra. Otherwise, the physician will now insert a sheath into the urethra and past the sphincter. The sheath is inserted into the prostatic urethra past the verumontanum until the forward end of the sheath reaches the lower end of the bladder neck. The stent is inserted, lower end first, into an accessory casing which has a lumen formed therein corresponding to the size of the lumen of the sheath in place in the urethra. As the stent is pushed into the lumen of the accessory casing, the conical flange will collapse. The accessory casing is then cooperatively aligned with the outer end of the sheath, and the stent is pushed out of the accessory casing and into the lumen of the sheath. The stent, with its conical flange now collapsed within the sheath, is pushed through the sheath with a flexible rod. As the stent emerges from the opposite end of the sheath, the conical flange will resile outwardly and engage the tapered walls of the bladder neck. If the stent is inadvertently pushed too far up the urethra, the physician can draw the stent back into place by grasping the filament and pulling.

Insertion of the sheath into the urethra may cause dilation of the urethra. Since the stent is dependent upon frictional contact between the textured outer surface of the stent and the urethral wall to maintain the stent in position, the patient must be kept still for several hours immediately following placement of the stent to permit the urethra to return to its normal state.

As will be appreciated by those of ordinary skill in the art, the stents 10, 30 must define a lumen of sufficient cross-sectional area to permit the uninterrupted flow of urine therethrough despite the occlusive pressure of an enlarged prostate. However, the provision of an open passage must be achieved within the parameters of a stent of sufficiently small outer diameter as not to surpass the ability of the urethra to expand to accommodate the stent without bleeding or undue pressure. In the disclosed embodiments, the inner diameter of the stent, that is, the diameter of the lumen, is approximately three millimeters, while the outer diameter of the stent body is six to seven millimeters. Since the urethra can easily accommodate a catheter of 24 french, or 8 mm, this outer diameter is easily within the range of plasticity of the prostatic urethra.

As has been shown, both embodiments 10, 30 of the present invention rely on the frictional force at the interface between the stent body and the walls of the urethra to anchor the stent against proximal migration into the bladder. Thus, the frictional force between the stent body and the urethral walls must be sufficient to resist the force exerted by the contraction of the smooth bladder neck musculature upon completion of micturition. As will be appreciated, frictional force is calculated by multiplying the contact surface area by the coefficient of friction between the stent and the urethral wall. Further, the coefficient of friction is a function of both the stent surface and the surface of the urethral wall with its mucosal lining. Because of the obvious difficulties in quantitatively measuring frictional characteristics of the urethral wall, an objective measurement of the coefficient of friction between the surface of the stent body and the urethral wall cannot easily be determined. However, this relationship may be functionally expressed in terms of a stent having a coefficient of friction with relation to a urethral wall which, when multiplied by the area of surface contact between the stent and the urethral wall, exerts a frictional force sufficient to resist the force exerted by the contraction of the smooth bladder neck musculature upon completion of micturition.

The present invention has been disclosed by way of a first embodiment comprising a spring-reinforced soft silicone rubber body having a cloth layer formed thereon and a second embodiment comprising a relatively high durometer inner liner having an outer jacket of softer silicone rubber formed thereon. However, it will be appreciated that the spring-reinforced soft silicone rubber body and the higher durometer inner liner are alternate means of accomplishing the same end, namely, the provision of a stent body which is sufficiently pliable to accommodate the natural anatomical bend of the prostatic urethra while being sufficiently strong to resist the radial stenotic pressures exerted by an enlarged prostate. Similarly, the textured fabric outer layer and the soft silicone jacket with roughened outer surface each comprise a means for frictionally engaging the slick walls of the urethra. Thus, it will be appreciated that these various elements may be combined in different combinations, such as a relatively high durometer inner liner having a textured cloth layer bonded thereto, or a spring-reinforced stent body having a roughened silicone outer layer formed thereon.

While the reinforcing spring element 28 of the stent 10 has been disclosed with respect to a steel spring, it will be appreciated that nylon or plastic spring elements may also provide the desired reinforcement characteristics. Also, while the reinforcing spring element has been disclosed with respect to a helical spring element, it will be appreciated that annular reinforcing elements in parallel, spaced-apart relation may also provide the necessary degree of reinforcement.

Finally, it will be understood that the preferred embodiment of the present invention is disclosed by way of example, and that other modifications may occur to those skilled in the art without departing from the scope and spirit of the appended claims.

What is claimed is:

1. An apparatus for the nonsurgical management of bladder outlet obstruction, comprising:
   an elongated body having an exterior surface, said body having first and second ends and defining a passage therethrough, said body being dimensioned to be received within a prostatic urethra and having a length sufficient to extend only from a bladder neck approximately to a verumontanum, and said body comprising an inner member of silicone rubber having a durometer hardness of about 80 on the Shore A scale and a concentric outer member of silicone rubber having a durometer hardness of about 40 on the Shore A scale, said outer member being bonded to said inner member, and said concentric outer member having an exterior surface comprising said exterior surface of said body;
   said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra; and
   high friction means on said exterior surface of said body for frictionally engaging the walls of said prostatic urethra to prevent said apparatus from migrating proximally;
   whereby when said apparatus is positioned within said prostatic urethra with said first end disposed at said bladder neck and said body extending approximately to said verumontanum, said body provides support to said prostatic urethra to ensure patency thereof.

2. An apparatus for the nonsurgical management of bladder outlet obstruction, comprising:
   an elongated body having an exterior surface, said body having first and second ends and defining a passage therethrough, said body being dimensioned to be received within a prostatic urethra and having a length sufficient to extend only from a bladder neck approximately to a verumontanum;
   said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra; and
   a fabric layer bonded to said exterior surface of said body for frictionally engaging the walls of said prostatic urethra to prevent said apparatus from migrating proximally;
   whereby when said apparatus is positioned within said prostatic urethra with said first end disposed at said bladder neck and said body extending approximately to said verumontanum, said body provides support to said prostatic urethra to ensure patency thereof.

3. An apparatus for the nonsurgical management of bladder outlet obstruction, comprising:
   an elongated body having an exterior surface, said body having first and second ends and defining a passage therethrough, said body being dimensioned to be received within a prostatic urethra and having a length sufficient to extend only from a bladder neck approximately to a verumontanum;
   said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra;
   high friction means on said exterior surface of said body for frictionally engaging the walls of said prostatic urethra to prevent said apparatus from migrating proximally; and
   a filament having one end secured to said body, whereby said filament may be manipulated to maneuver said apparatus to a desired location within said prostatic urethra;
   whereby when said apparatus is positioned within said prostatic urethra with said first end disposed at said bladder neck and said body extending approximately to said verumontanum, said body provides support to said prostatic urethra to ensure patency thereof.

4. An apparatus for the nonsurgical management of bladder outlet obstruction, comprising:
   an elongated body having an exterior surface, said body having first and second ends and defining a passage therethrough, said body being dimensioned to be received within a prostatic urethra and having a length sufficient to extend only from a bladder neck approximately to a verumontanum, said body comprising an inner member of silicone rubber having a durometer hardness of about 80 on the Shore A scale and concentric outer member of silicone rubber having a durometer hardness of about 40 on the Shore A scale bonded to said inner member, said concentric outer member having an exterior surface comprising said exterior surface of said body;

said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra; and said exterior surface of said body having a coefficient of friction with relation to a urethral wall which, when multiplied by an area of surface contact between said exterior surface of said body and said urethral wall, exerts a frictional force sufficient to resist a force exerted by a contraction of smooth bladder neck musculature upon completion of micturition to prevent said apparatus from migrating proximally;

whereby when said apparatus is positioned within said prostatic urethra with said first end of said body disposed at said bladder neck and said body extending approximately to said verumontanum, said body provides support to said prostatic urethra to ensure patency thereof.

5. An apparatus for the nonsurgical management of bladder outlet obstruction, comprising:

an elongated body having an exterior surface, said body having first and second ends and defining a passage therethrough, said body being dimensioned to be received within a prostatic urethra and having a length sufficient to extend only from a bladder neck approximately to a verumontanum;

said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra; and a fabric layer bonded to said exterior surface of said body and having a coefficient of friction with relation to a urethral wall which, when multiplied by an area of surface contact between said fabric layer and said urethral wall, exerts a frictional force sufficient to resist a force exerted by a contraction of smooth bladder neck musculature upon completion of micturition to prevent said apparatus from migrating proximally;

whereby when said apparatus is positioned within said prostatic urethra with said first end of said body disposed at said bladder neck and said body extending approximately to said verumontanum, said body provides support to said prostatic urethra to ensure patency thereof.

6. An apparatus for the nonsurgical management of bladder outlet obstruction, comprising:

an elongated body having an exterior surface, said body having first and second ends and defining a passage therethrough, said body being dimensioned to be received within a prostatic urethra and having a length sufficient to extend only from a bladder neck approximately to a verumontanum;

said body being sufficiently flexible to accommodate an anatomical bend of said prostatic urethra and sufficiently stiff to maintain patency of said passage in response to accommodation of said anatomical bend of said prostatic urethra and in response to constrictive forces exerted by an enlarged prostate surrounding said prostatic urethra;

said exterior surface of said body having a coefficient of friction with relation to a urethral wall which, when multiplied by an area of surface contact between said exterior surface of said body and said urethral wall, exerts a frictional force sufficient to resist a force exerted by a contraction of smooth bladder neck musculature upon completion of micturition to prevent said apparatus from migrating proximally; and a filament having one end secured to said body, whereby said filament may be manipulated to maneuver said apparatus to a desired location within said prostatic urethra;

whereby when said apparatus is positioned within said prostatic urethra with said first end of said body disposed at said bladder neck and said body extending approximately to said verumontanum, said body provides support to said prostatic urethra to ensure patency thereof.

* * * * *